United States Patent
Bi

(10) Patent No.: US 8,813,542 B1
(45) Date of Patent: Aug. 26, 2014

(54) HIGH PRESSURE VESSEL WITH MOVABLE PRESSURIZATION PISTON

(76) Inventor: Hongfeng Bi, Houston, TX (US)

(*) Notice: Subject to any disclaimer, the term of this patent is extended or adjusted under 35 U.S.C. 154(b) by 116 days.

(21) Appl. No.: 13/317,891

(22) Filed: Oct. 31, 2011

(51) Int. Cl.
*G01N 11/14* (2006.01)
*G01N 11/10* (2006.01)

(52) U.S. Cl.
USPC .......................................... 73/54.28; 73/54.23

(58) Field of Classification Search
CPC ........ G01N 11/02; G01N 11/10; G01N 11/14
USPC ................... 73/54.28, 54.01–54.42
See application file for complete search history.

(56) References Cited

U.S. PATENT DOCUMENTS

| 3,492,857 | A | * | 2/1970 | Barnett et al. ............... 73/54.01 |
| 4,461,937 | A |   | 7/1984 | Boni |
| 5,211,532 | A |   | 5/1993 | Thompson |
| 5,666,012 | A | * | 9/1997 | Gongwer ........................ 310/87 |
| 5,770,795 | A | * | 6/1998 | Behar et al. .................. 73/54.23 |
| 7,287,415 | B2 |  | 10/2007 | Borwick, III et al. |
| 7,287,416 | B1 |  | 10/2007 | Bi |
| 7,289,873 | B2 | * | 10/2007 | Redecker et al. ............. 700/174 |

\* cited by examiner

*Primary Examiner* — Daniel S Larkin
*Assistant Examiner* — Irving A Campbell

(57) ABSTRACT

Viscometer (150) with a rotor (108) connecting a magnet holder (62) which penetrates a sealed movable piston (96) and rotatable by a coupling magnet (58) and a driving magnet (64) to shear a tested fluid thus imparting torque to a bob (42) mounted on a bob shaft (30) supported via a pair of bob shaft bearings. A spiral spring (140) restricts the rotation of bob shaft (30). Magnetometer (10) measures the angular position of a top magnet (142) connected to the top of bob shaft (30). This angular position information is further converted to the viscosity of the tested fluid.

20 Claims, 3 Drawing Sheets

DETAIL 43A

DETAIL 43B

HIGH PRESSURE VESSEL WITH MOVABLE PRESSURIZATION PISTON

BACKGROUND

1. Field of Invention

Figure 1:
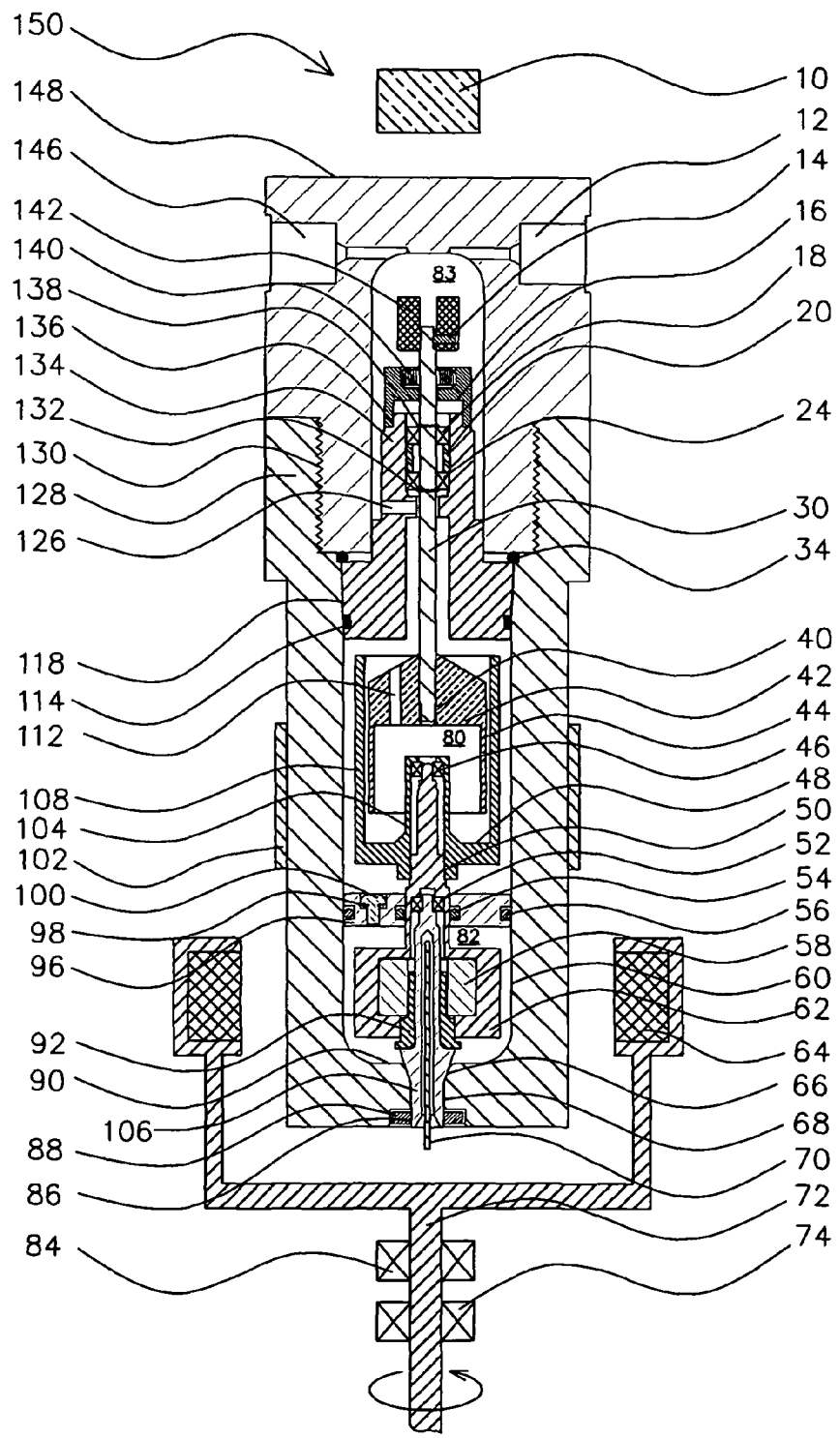

The present invention relates to a low-maintenance high-pressure viscometer which includes a pressure vessel containing a movable piston assembly which separates a test sample from a pressurization fluid. The piston assembly also allows for the transfer of torque into the test sample by means of a rotatable shaft extending through the piston, while maintaining the required seal integrity of all chambers under conditions of temperature and pressure conducive to high-pressure, high-temperature viscosity tests.

2. Description of Prior Art

In connection with the drilling of oil and gas wells, drilling fluid is commonly used to drive the drill bit and bring sand and stone cuttings back to ground surface. The viscosity property of drilling fluid is critical in the drilling process. A drilling fluid with excessive viscosity would make it difficult to pump it down to the bore hole, while a drilling fluid with insufficient viscosity would make it difficult to carry sand and stone cuttings back to ground surface. The viscosity property of a drilling fluid varies significantly with the change of temperature and pressure. Thus a viscometer capable of closely simulating down-hole conditions with low maintenance is of great interest. Down-hole conditions are typically from room temperature and pressure up to 40,000 psi and 600° F.

U.S. Pat. No. 7,287,416—LOW MAINTENANCE HIGH PRESSURE VISCOMETER teaches a viscometer which meets these criteria to a great degree, but allows the test sample to come into direct contact with a magnet. This would prevent the accurate measurement of many high-density drilling muds because hematite is a common component of most high-density drilling muds. Hematite materials in high-density muds would be attracted to the magnet, thus causing inaccurate measurement. Prior art U.S. Pat. No. 7,287,415 also does not allow the testing of corrosive samples that would react with the magnet.

It is an object of this invention to provide a high-pressure viscometer wherein viscosity is determined under conditions closely simulating down-hole conditions.

It is another object of this invention to provide a high-pressure viscometer that provides a plurality of pressurizable test chambers.

It is another object of this invention to provide a high-pressure viscometer that provides a testing environment in which tested sample is kept entirely isolated and uncontaminated.

It is another object of this invention to provide a viscometer that requires substantially less maintenance work yet meets industry standards of accuracy, repeatability, durability, and ease of cleaning.

SUMMARY

A viscometer in accord with the present invention conveniently comprises a pressure vessel inside which a rotor is suspended and a magnetic coupling for rotating the rotor. Suspended within the rotor is a bob capable of angular motion about the longitudinal axis of the rotor. The device is constructed so that the bob and the rotor are immersed within the test liquid, the viscosity of which is to be determined. This test liquid is kept separated from the magnetic coupling by a sealed piston. A rotating shaft extends through the piston without violating the integrity of the seal.

The bob is suspended within the pressure vessel by a pair of low friction ball bearings and a bob shaft. A spiral spring permits limited angular motion of the bob shaft. A magnet is secured on top of the bob shaft. A magnetometer located on the top of the pressure vessel senses the rotation of the magnet. The apparatus and method of the present invention provide a way to measure the shear stress property of fluid under shear condition.

DRAWING FIGURES

Figure 2:
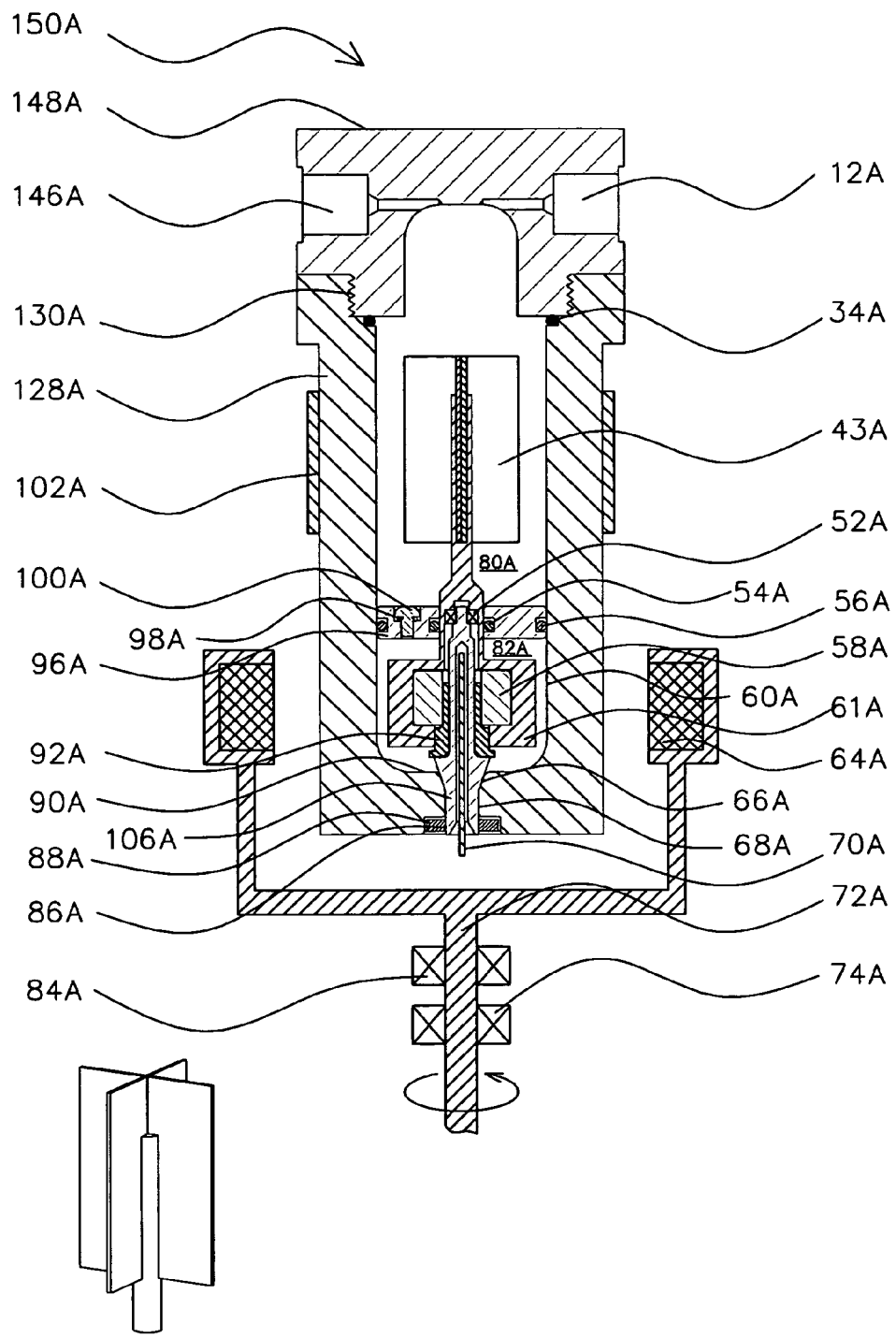
Figure 3:
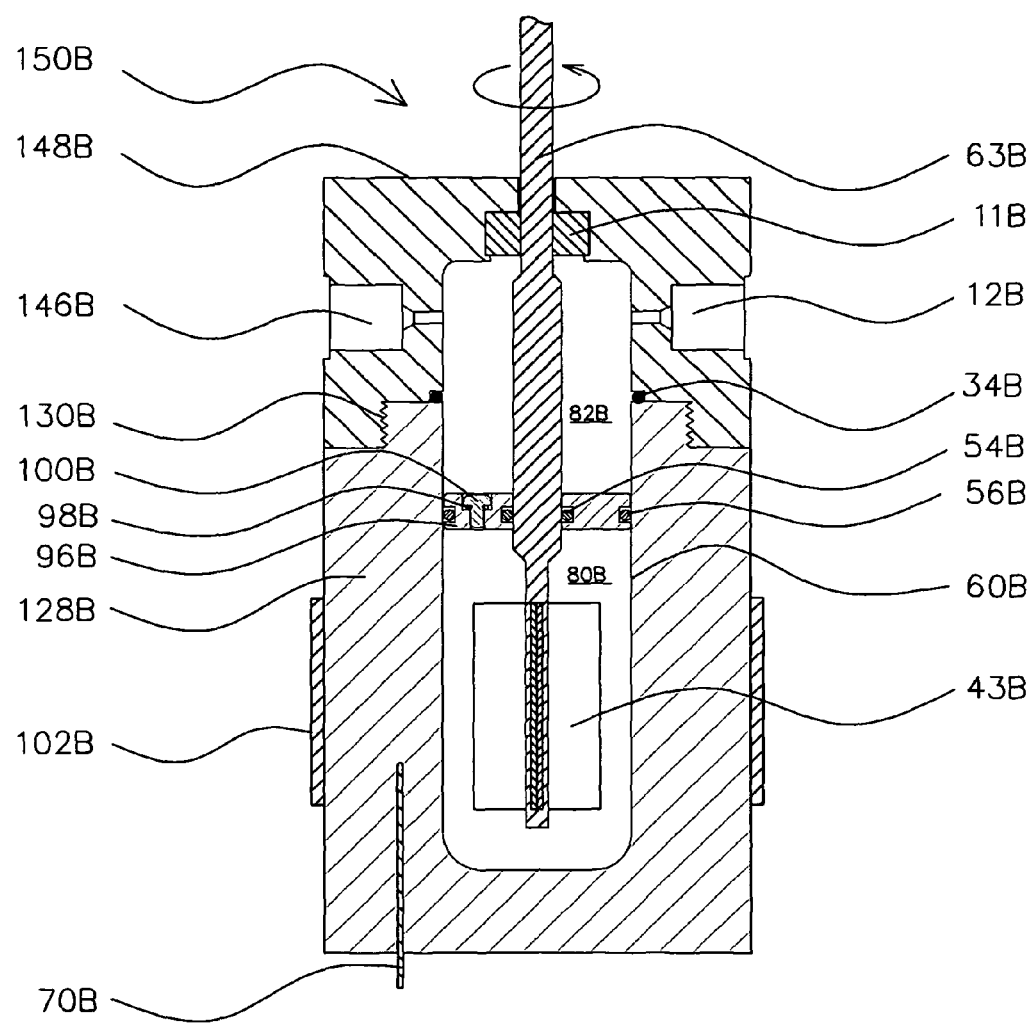
Figure 3:
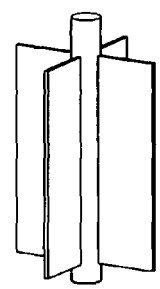

Other objects, features and advantages will be apparent from the following detailed description of preferred embodiments taken in conjunction with accompanying drawing in which:

FIG. 1 is a cross-section view of a preferred viscometer embodiment of the invention, FIG. 2 is a cross-section view of a second configuration of the viscometer embodiment of the invention, and FIG. 3 is a cross-section view of a third viscometer/reactor embodiment of the invention.

| Reference Numerals in Drawings | | | |
|---|---|---|---|
| 10 | magnetometer | 11B | dynamic seal |
| 12 | inlet | 12A | inlet |
| 12B | inlet | 14 | set screw |
| 16 | spring holder | 18 | bob shaft bearing |
| 20 | bearing spacer | 24 | bob shaft bearing |
| 30 | bob shaft | 34 | o-ring |
| 34A | o-ring | 34B | o-ring |
| 40 | screw thread | 42 | bob |
| 43A | spindle | 43B | spindle |
| 44 | small gap | 46 | support bearing |
| 48 | rotor bottom | 50 | flat surface |
| 52 | bearing | 52A | bearing |
| 54 | o-ring | 54A | o-ring |
| 54B | o-ring | 56 | o-ring |
| 56A | o-ring | 56B | o-ring |
| 58 | magnet | 58A | magnet |
| 60 | cell wall | 60A | cell wall |
| 60B | cell wall | 62 | magnet holder |
| 63B | shaft | 64 | driving magnet |
| 64A | driving magnet | 66 | conical surface |
| 66A | conical surface | 68 | straight bore |
| 68A | straight bore | 70 | thermal couple |
| 70A | thermal couple | 72 | magnet mount |
| 72A | magnet mount | 74 | bearing |
| 74A | bearing | 80 | sample fluid |
| 80A | sample fluid | 80B | sample fluid |
| 82 | pressurization fluid | 82A | pressurization fluid |
| 82B | pressurization fluid | 83 | top pressurization fluid |
| 84 | bearing | 84A | bearing |
| 86 | thread | 86A | thread |
| 88 | lock nut | 88A | lock nut |
| 90 | cell bottom | 90A | cell bottom |
| 92 | bushing - | 92A | bushing |
| 96 | piston | 96A | piston |
| 96B | piston | 98 | o-ring |
| 98A | o-ring | 98B | o-ring |
| 100 | screw | 100A | screw |
| 100B | screw | 102 | heater |
| 102A | heater | 102B | heater |
| 104 | rotor inside wall | 106 | pivot |
| 106A | pivot | 108 | rotor |
| 112 | bob vent | 114 | o-ring |
| 118 | conical surface | 126 | venting hole |
| 128 | cell body | 128A | cell body |
| 128B | cell body | 130 | screw thread |
| 130A | screw thread | 130B | screw thread |
| 132 | snap ring | 134 | bearing holder |
| 136 | flat | 138 | snap ring |
| 140 | spiral spring | 142 | top magnet |
| 146 | outlet | 146A | outlet |
| 146B | outlet | 148 | cell cap |

Reference Numerals in Drawings

| 148A | cell cap | 148B | cell cap |
|------|----------|------|----------|
| 150  | viscometer | 150A | viscometer |
| 150B | viscometer/reactor | | |

Description—FIG. 1

Preferred Embodiment

FIG. 1 is a cross-section view of a viscometer 150 with a cell body 128 and a cell cap 148. Cell body 128 is detachable from cell cap 148 via a screw thread 130. An o-ring 34 assures against the escape of fluid through screw thread 130. Inside of cell body 128 and below screw thread 130 is a conical surface 118 with reduced diameter, below which cell body 128 extends downward to a cell wall 60 and then further downward to a cell bottom 90. A tapered hole with a conical surface 66 and a straight bore 68 is located in the center of cell bottom 90. A pivot 106, which is secured to cell bottom 90 by a lock nut 88 through a thread 86, is seated into said tapered hole on conical surface 66. Lock nut 88 is tightened to provide initial seal on conical surface 66 between cell bottom 90 and pivot 106. A thermal couple 70 is inserted into the center of pivot 106. Radially outward of the outer surface of pivot 106 is a bushing 92. Bushing 92 is made of Rulon, Teflon or equivalent plastic. A magnet holder 62 and a magnet 58 are positioned radially outward of bushing 92. A bearing 52 provides vertical support of magnet holder 62 and magnet 58, which can rotate on the same central axis of pivot 106.

A piston 96 is positioned above magnet holder 62 and consists of a disk with two through holes, one centered and one off-centered. An o-ring 56 is installed onto the outer edge of piston 96 and forms a liquid-tight seal with cell wall 60. An o-ring 54 is also installed onto the inner edge of the centered hole in piston 96 and forms a liquid-tight seal with magnet holder 62. A screw 100 is installed into the off-centered hole in piston 96 and is sealed against leakage with an o-ring 98.

A rotor 108 is positioned radially outward of magnet holder 62. A support bearing 46 provides vertical support of rotor 108, which can rotate on the same central axis of magnet holder 62. Rotor 108 consists of a disc-shaped rotor bottom 48 and a hollow cylindrical rotor inside wall 104, which fits together with a flat surface 50 on magnet holder 62, so that rotation by magnet holder 62 causes rotor 108 to rotate also.

A bearing holder 134 is positioned near the top of cell body 128 and consists of a conical section and two different outside diameter sections. The outer surface of the conical section of bearing holder 134 mates inside conical surface 118 of cell body 128. An o-ring 114 provides a liquid-tight seal on conical surface 118. A bob shaft 30 passes through the center of bearing holder 134 and is rotationally supported by a bob shaft bearing 18, a bob shaft bearing 24, a bearing spacer 20, a snap ring 138 and a snap ring 132. A bob 42 is screwed on the bottom of bob shaft 30 via a screw thread 40 and is submerged in a sample fluid 80. A bob vent 112 is provided along the axial direction of bob 42 connecting the inside vacancy of bob 42 to its top. There is a small gap 44 between bob 42 and rotor 108.

A machined flat 136 is provided on the top of bearing holder 134. Mating and resting on flat 136 is a spring holder 16. A spiral spring 140 is placed in the center of spring holder 16 so that the outside lead of spiral spring 140 is fixed to the inside counter bore of spring holder 16 and the inside lead of spiral spring 140 is fixed to bob shaft 30 with any conventional means. A horseshoe-type top magnet 142 is fixed to the top of bob shaft 30 with a set screw 14. A venting hole 126 can communicate fluids between the outer surface and the center of bearing holder 134.

An inlet 12 and an outlet 146 provide ports for injecting and expelling a top pressurization fluid 83. A magnetometer 10 located on the top of cell cap 148 can measure the rotational displacement of top magnet 142.

A magnet mount 72 is rotationally supported on the outside of cell body 128 by a bearing 74 and a bearing 84. Magnet mount 72 can be rotated by any conventional means such as a gear box or motor. A pair of driving magnet 64 is mounted on magnet mount 72 at considerably the same level where magnet 58 is mounted inside of cell body 128. A heater 102 heats up cell body 128 while thermal couple 70 provides temperature feedback for temperature control. Magnet 58, positioned inside magnet holder 62, is submerged in a pressurization fluid 82.

Operation—FIG. 1

Preferred Embodiment

To assemble viscometer 150, pivot 106 is lowered into cell body 128 and inserted into conical surface 66 and straight bore 68, then secured to cell bottom 90 by lock nut 88 via thread 86. Pivot 106 can be cleaned together with cell body 128.

Bushing 92 is pushed into magnet holder 62 bottom, which also contains magnet 58 and bearing 52. This said subassembly is dropped into cell body 128 and rotationally supported by bearing 52 resting on pivot 106. Pressurization fluid 82 is poured into cell body 128. O-ring 56 and o-ring 54 are installed onto piston 96. Piston 96 is then dropped into cell body 128 so that o-ring 54 forms a seal with magnet holder 62 and o-ring 56 forms a seal with cell wall 60. When piston 96 is at the proper position, screw 100 and o-ring 98 are installed. Support bearing 46 is installed into rotor 108, and rotor 108 is lowered onto the upper stem of magnet holder 62, where it mates with flat surface 50. Sample fluid 80 is poured into cell body 128 so that sample surface just submerges the top of rotor 108.

Holding bob shaft 30 in hand, install bob shaft bearing 18, bearing spacer 20, bob shaft bearing 24, snap ring 138 and snap ring 132 onto bob shaft 30. Then vertically insert this subassembly into bearing holder 134. Next, install spring holder 16 and spiral spring 140 onto the top of bearing holder 134 by mating it with flat 136. Install top magnet 142 to the top of bob shaft 30 and secure with set screw 14. Screw bob 42 onto bob shaft 30 bottom via screw thread 40. Install o-ring 114 onto the outer surface of bearing holder 134. Slowly push this bob shaft holder assembly vertically down into cell body 128.

As the bob shaft holder assembly descends into cell body 128, bob 42 descends to a position above rotor bottom 48, and air trapped inside of bob 42 is vented through bob vent 112. Bob 42 also expels the sample fluid 80 causing sample fluid 80 level to rise. This expelled volume is stopped by o-ring 114 and can only cause the level of sample fluid 80 to rise inside of bearing holder 134. Consequently, bearing holder 134 is partially filled with sample fluid 80 after the bearing holder assembly has formed a seal with o-ring 114 on cell body 128 against conical surface 118.

Screw down cell cap 148 onto screw thread 130 with o-ring 34 in place. Pump top pressurization fluid 83 from inlet 12 until all air inside of pressure vessel is expelled out through outlet 146. Sample testing pressure can be raised by pumping more top pressurization fluid 83 into the pressure vessel through inlet 12 or lowered by releasing some top pressurization fluid 83 from the pressure vessel via outlet 146.

It is very important to have rotor 108 and bob 42 concentrically aligned. Conical surface 118 is machined with high precision to ensure that bob 42 is concentrically aligned with rotor 108. This conical surface 118 also significantly simplifies the installation process since no additional adjustment or screw turning is required to ensure the good concentricity between rotor 108 and bob 42.

A motor or gearbox drives magnet mount 72 to rotate on bearing 74 and bearing 84 carrying driving magnet 64. Heater 102 heats up cell body 128 while thermal couple 70 provides temperature feedback for temperature control. Due to the magnetic coupling between driving magnet 64 and magnet 58, and the configuration of rotor 108 fitting together with flat surface 50 on magnet holder 62, rotor 108 rotates at the same revolving speed as magnet mount 72 does. Because of the viscosity of sample fluid 80, a torque is generated on bob 42 causing it to rotate. Because of spiral spring 140, the rotation angle of bob shaft 30 is roughly proportional to the torque applied on bob 42. Magnetometer 10 picks up the rotation angle of top magnet 142 which rotates with bob shaft 30. The rotation angle in turn can be used to calculate the viscosity of sample fluid 80.

One of the drawbacks of some liquid pressurized viscometers is that sample fluid is allowed to contact a magnet directly. This contact might cause a magnetic reaction in the sample fluid which interferes with test operations and prevents accurate measurement.

In the current invention, sample fluid 80 is kept completely free of contact with magnet 58. Magnet 58, inside magnet holder 62, is submerged in a pressurization fluid 82. Piston 96 is placed onto magnet holder 62 so that it seals the lower portion of cell body 128 completely, with o-ring 54 and o-ring 56 assuring against leakage. Sample fluid 80 can then be introduced into the upper part of cell body 128 without allowing sample fluid 80 to come into contact with magnet 58.

Description—FIG. 2

Second Embodiment

FIG. 2 is a cross-section view of viscometer 150A with a cylindrical cell body 128A and a cell cap 148A. Cell body 128A is detachable from cell cap 148A via a screw thread 130A. An o-ring 34A assures against the escape of fluid through screw thread 130A. Inside of cell body 128A and below screw thread 130A is a cell wall 60A, below which cell body 128A extends downward to a cell bottom 90A. A tapered hole with a conical surface 66A and a straight bore 68A is located in the center of cell bottom 90A. A pivot 106A, which is secured to cell bottom 90A by a lock nut 88A through a thread 86A, is seated into said tapered hole on conical surface 66A. Lock nut 88A is tightened to provide initial seal on conical surface 66A between cell bottom 90A and pivot 106A. A thermal couple 70A is inserted into the center of pivot 106A. Radially outward of the outer surface of pivot 106A is a bushing 92A. Bushing 92A is made of Rulon, Teflon or equivalent plastic. A magnet holder 61A and a magnet 58A are positioned radially outward of bushing 92A. A bearing 52A provides vertical support of magnet holder 61A and magnet 58A, which can rotate on the same central axis of pivot 106A. A spindle 43A is attached to the top of magnet holder 61A and rotates on the same axis of pivot 106A.

A piston 96A is positioned radially outward of magnet holder 61A and consists of a disk perforated by two holes, one centered and one off-centered, an o-ring 56A, an o-ring 54A, a screw 100A and an o-ring 98A. O-ring 56A is installed onto the outer edge of piston 96A and forms a liquid-tight seal with cell wall 60A. O-ring 54A is installed onto the inner edge of the centered hole in piston 96A and forms a liquid-tight seal with magnet holder 61A. Screw 100A is installed into the off-centered hole in piston 96A and is sealed against leakage with o-ring 98A.

An inlet 12A and an outlet 146A provide ports for injecting and releasing a sample fluid 80A. A magnet mount 72A is rotationally supported on the outside of cell body 128A by a bearing 74A and a bearing 84A. Magnet mount 72A can be rotated by any conventional means such as a gear box or motor. A pair of driving magnet 64A is mounted on magnet mount 72A at considerably the same level where magnet 58A is mounted inside of the cell body 128A. A heater 102A heats up cell body 128A while thermal couple 70A provides temperature feedback for temperature control. Spindle 43A is immersed in sample fluid 80A. As spindle 43A turns, it stirs sample fluid 80A.

A motor or gearbox drives magnet mount 72A to rotate on bearing 74A and bearing 84A carrying driving magnet 64A. Due to the magnetic coupling between driving magnet 64A and magnet 58A, and the attachment of spindle 43A to magnet holder 61A, spindle 43A rotates at the same revolving speed as magnet mount 72A does. Because of the viscosity of sample fluid 80A, a torque is generated on magnet mount 72A. The measurement of this torque can be used to calculate the viscosity of sample fluid 80A.

In the current invention, sample fluid 80A is kept completely free of contact with magnet 58A. Magnet 58A, positioned inside magnet holder 61A, is submerged in a pressurization fluid 82A. Piston 96A is placed onto magnet holder 61A so that it seals the lower portion of cell body 128A completely, with o-ring 54A and o-ring 56A assuring against leakage. Sample fluid 80A can then be introduced into the upper part of cell body 128A through sample inlet 12A, without allowing sample fluid 80A to come into contact with magnet 58A.

Operation—FIG. 2

Second Embodiment

To assemble viscometer 150A, Pivot 106A is inserted into conical surface 66A and straight bore 68A and secured to cell bottom 90A by lock nut 88A through thread 86A. Pivot 106A can be cleaned together with cell body 128A. Bushing 92A is pushed into magnet holder 61A, which also contains magnet 58A and bearing 52A. This said subassembly is dropped into cell body 128A and rotationally supported by bearing 52A resting on pivot 106A. Pressurization fluid 82A is poured into cell body 128A. O-ring 52A and o-ring 54A are installed onto piston 96A. Piston 96A is then dropped into cell body 128A so that o-ring 54A forms a seal with magnet holder 61A and o-ring 56A forms a seal with cell wall 60A. When piston 96A is at the proper position, screw 100A and o-ring 98A are installed. Attach spindle 43A to the top of magnet holder 61A.

Screw down cell cap 148A onto screw thread 130A with o-ring 34A in place. Pump sample fluid 80A from inlet 12A until all air inside of pressure vessel is expelled out through outlet 146A. Sample testing pressure can be raised by pumping more sample fluid 80A into the pressure vessel or lowered by releasing some sample fluid 80A from the pressure vessel.

A motor or gearbox drives magnet mount 72A to rotate on bearing 74A and bearing 84A carrying driving magnet 64A. Heater 102A heats up cell body 128A while thermal couple 70A provides temperature feedback for temperature control. Due to the magnetic coupling between driving magnet 64A and magnet 58A, spindle 43A rotates at the same revolving speed as magnet mount 72A does. Because of the viscosity of sample fluid 80A, a torque is generated on magnet mount 72A. The measurement of this torque can be used to calculate the viscosity of sample fluid 80A.

One of the drawbacks of some liquid pressurized viscometers is that sample fluid is allowed to contact a magnet directly. This contact might cause a magnetic reaction in the sample fluid which interferes with test operations and prevents accurate measurement. Another drawback of most liquid pressurized viscometers is the mixing between sample fluid and pressurization fluid. If pressurization fluid is allowed to contact sample fluid directly, pressurization fluid will mix with sample fluid, introducing the possibility of invalid test results.

In the current invention, sample fluid 80A is kept completely free of contact with magnet 58A as well as pressurization fluid 82A. Magnet 58A, inside magnet holder 61A, is submerged in pressurization fluid 82A. Piston 96A is placed onto magnet holder 61A so that it seals the lower portion of cell body 128A completely, with o-ring 54A and o-ring 56A assuring against leakage. Sample fluid 80A can then be introduced into the upper part of cell body 128A by pouring as well as through inlet 12A without allowing sample fluid 80A to come into contact with magnet 58A or pressurization fluid 82A.

Description—FIG. 3

Viscometer/Reactor Embodiment

FIG. 3 is a cross-section view of viscometer/reactor 150B with a cylindrical cell body 128B and a cell cap 148B. Cell body 128B is detachable from cell cap 148B via a screw thread 130B. An o-ring 34B assures against the escape of fluid through screw thread 130B. Inside of cell body 128B and below screw thread 130B is a cell wall 60B.

A shaft 63B extends through cell cap 148B and into cell body 128B. A dynamic seal 11B mounted inside cell cap 148B assures against leakage. Shaft 63B can be rotated by a gearbox or any conventional method.

A piston 96B is positioned radially outward of shaft 63B and consists of a disk perforated by two holes, one centered and one off-centered, an o-ring 56B, an o-ring 54B, a screw 100B and an o-ring 98B. O-ring 56B is installed onto the outer edge of piston 96B and forms a liquid-tight seal with cell wall 60B. O-ring 54B is installed onto the inner edge of the centered hole in piston 96B and forms a liquid-tight seal with shaft 63B. Screw 100B is installed into the off-centered hole in piston 96B and is sealed against leakage with o-ring 98B. A spindle 43B is attached to shaft 63B inside cell body 128B and below piston 96B.

An inlet 12B and an outlet 146B provide ports for injecting and releasing a pressurization fluid 82B, which fills the area of cell body 128B above piston 96B. Sample fluid 80B fills the area of cell body 128B below piston 96B, immersing spindle 43B. A heater 102B heats up cell body 128B while thermal couple 70B is inserted into cell body 128B and provides temperature feedback for temperature control.

A motor or gearbox drives shaft 63B to rotate, causing attached spindle 43B to rotate as well. Due to the attachment of spindle 43B to shaft 63B, spindle 43B rotates at the same revolving speed as shaft 63B does. Because of the viscosity of sample fluid 80B, a torque is generated on shaft 63B. The measurement of this torque can be used to calculate the viscosity of sample fluid 80B.

Operation—FIG. 3

Viscometer/Reactor Embodiment

To assemble viscometer/reactor 150B, sample fluid 80B is poured into cell body 128B. O-ring 54B and o-ring 56B are installed onto piston 96B. Spindle 43B is attached to shaft 63B. Shaft 63B is then passed through piston 96B so that o-ring 54B forms a liquid-tight seal with shaft 63B. Piston 96B is then dropped into cell body 128B until o-ring 56B forms a liquid-tight seal with cell wall 60B. When piston 96B is positioned inside cell body 128B so that there is no air between piston 96B and sample fluid 80B, screw 100B and o-ring 98B are installed into piston 96B.

Dynamic seal 11B is installed into cell cap 148B. O-ring 34B is installed onto the top of cell body 128B. Cell cap 148B is then lowered onto cell body 128B and screwed onto screw thread 130B so that o-ring 34B assures against leakage and shaft 63B passes through dynamic seal 11B.

Pressure is introduced into viscometer/reactor 150B by pressurization fluid 82B, which is injected through inlet 12B into cell body 128B and said pressure can be removed by ejecting pressurization fluid 82B through outlet 146B. Heater 102B heats up cell body 128B while thermal couple 70B provides temperature feedback for temperature control.

Due to the attachment of spindle 43B to shaft 63B, spindle 43B rotates at the same revolving speed as shaft 63B does. Because of the viscosity of sample fluid 80B, a torque is generated on spindle 43B and this torsion is passed on to shaft 63B. The measurement of this torque can be used to calculate the viscosity of sample fluid 80B.

Ramifications

In FIG. 1, top pressurization fluid 83 can be replaced with 80 sample fluid to pressurize pressure vessel assembly.

In FIG. 1, top pressurization fluid 83 can be either gas or liquid.

In FIG. 2, spindle 43A can be cylindrical, disc or other shapes without affecting current invention principles.

In FIG. 3, spindle 43B can be cylindrical, disc or other shapes without affecting current invention principles.

In FIG. 2, viscometer 150A can be turned and operated horizontally or at other angles without affecting its operation.

In FIG. 3, viscometer/reactor 150B can be turned and operated horizontally or at other angles without affecting its operation.

In FIG. 1, piston 96 can be made of sealing material such as Teflon or PEEK, thus eliminating the need for o-ring 54 and o-ring 56.

In FIG. 2, piston 96A can be made of sealing material such as Teflon or PEEK, thus eliminating the need for o-ring 54A and o-ring 56A.

In FIG. 3, piston 96B can be made of sealing material such as Teflon or PEEK, thus eliminating the need for o-ring 54B and o-ring 56B.

In FIG. 1, spiral spring 140 can be helical type or other type as well.

In FIG. 1, there are many other ways to measure the angular displacement of bob shaft 30. For example, in the preferred embodiment viscometer 150, top magnet 142 and magnetometer 10 can be replaced with a pair of concentrically mounted electrical stator and rotor to measure the rotation of bob shaft 30. Additionally, top magnet 72 and magnetometer 10 can be replaced with an encoder to measure the rotation of bob shaft 30. A potentiometer and a brush attached to bob shaft 30 could measure the rotation as well. Alternatively, a metal arm or wiper which rotates with bob shaft 10, and a wire-wound conductance transducer which is mounted directly or indirectly on bearing holder 134 or cell cap 148, can also be used to measure the rotation of bob shaft 30 by measuring the conductance change in the wire-wound coil.

In FIG. 2, torque on spindle 43A can be measured in many ways, such as but not limited to, measurement of the power consumption of the driving device or motor assembly, direct measurement of torque on magnet mount 72A, etc.

In FIG. 3, torque on shaft 63B can be measured in many ways, such as but not limited to, measurement of the power consumption of the driving device or motor assembly, direct measurement of torque on shaft 63B, etc.

In FIG. 1, the hole in piston 96 through which magnet holder 62 extends does not have to be located in the center of piston 96.

In FIG. 2, the hole in piston 96A through which magnet holder 61A extends does not have to be located in the center of piston 96A.

In FIG. 3, the hole in piston 96B through which shaft 63B extends does not have to be located in the center of piston 96B.

Conclusion and Scope

Accordingly, the reader will see that this invention can be used to construct a high pressure viscometer that prevents contact between testing sample and driving magnet while providing continuous highly accurate measurement. This moving piston with a central rotating shaft configuration can also be easily used in a high pressure reactor.

Objects and Advantages

From the description above, a number of advantages of my viscometer become evident:

(a) Traditionally, magnetic drive is extensively used in transferring rotational energy into high pressure vessels due to the difficulties of using dynamic seals and the problem of friction with dynamic seals. Ordinarily, a magnetic drive design means that the coupling magnet inside of the pressure vessel would be in direct contact with the tested sample. My invention solves this problem by adding a movable piston with a dynamic seal in the said piston center. Also, due to the low pressure difference between the two sides of the moving piston, the friction on the piston dynamic seal is very small.

(b) The current invention allows the coupling magnet inside of the pressure vessel to contact only an inert pressurization fluid. This extends the magnet life substantially.

Further objects and advantages of my invention will become apparent from a consideration of the drawings and ensuing description.

What I claimed:

1. A pressurized device comprising:
   (a) a pressure vessel,
   (b) a movable piston without fluid passing through its center inside of said pressure vessel dividing said pressure vessel into at least one chamber filled with a pressurization fluid and one chamber filled with a sample,
   (c) a seal means in contact with said movable piston and said pressure vessel,
   (d) a rotating shaft at least partially located inside of said pressure vessel,
   (e) a hole in said movable piston allowing said rotating shaft to pass through said movable piston,
   (f) another seal in contact with said movable piston and said rotating shaft that prevents fluid exchange between said chamber filled with a pressurization fluid and said chamber filled with a sample,
   (g) a magnetic drive means to drive said rotating shaft to rotate, whereas wherein at least one magnet of said magnetic drive means is located inside said chamber filled with said pressurization fluid.

2. The pressurized device of claim 1, wherein the pressurized device is a reactor.

3. The pressurized device of claim 1, wherein at least one magnet of said magnetic drive means is connected to said rotating shaft.

4. The pressurized device of claim 1, wherein said magnetic drive means further comprises a coupling magnet located outside of said pressure vessel, while coupling with said magnet.

5. The pressurized device of claim 1 further comprising a means to add or subtract said pressurization fluid to or from said pressure vessel.

6. The pressurized device of claim 1 further comprising a means to add or subtract said sample to or from said pressure vessel.

7. The pressurized device of claim 1, wherein the pressurized device is a viscometer.

8. A viscometer instrument comprising:
   (a) a pressure vessel,
   (b) a rotor within said pressure vessel which is driven to rotate while in contact with a sample liquid to be measured,
   (c) a means for driving said rotor to rotate,
   (d) a bob within said rotor,
   (e) a means to measure torque applied on said bob due to fluid viscosity,
   (f) a movable piston without fluid passing through its center inside of said pressure vessel with one chamber in contact with said sample liquid and another chamber filled with a pressurization fluid,
   (g) a rotating shaft that rotates together with said rotor,
   (h) a hole in said movable piston allowing said rotating shaft to pass through said movable piston,
   (i) a magnetic drive means to drive said rotating shaft to rotate, wherein at least one magnet of said magnetic drive means is located inside of said chamber filled with said pressurization fluid.

9. A viscometer according to claim 8 further comprising a bearing means for rotationally suspending said bob.

10. A viscometer according to claim 8 further comprising a spring means restricting the rotation of said bob.

11. A viscometer according to claim 10 wherein said spring means is a spiral spring.

12. A viscometer according to claim 10 wherein said spring means is a helical spring.

13. A viscometer according to claim 8 further comprising a means for directly or indirectly sensing the rotation of said bob.

14. A viscometer according to claim 13 wherein said means for directly or indirectly sensing the rotation of said bob consist of a magnet and a magnetometer.

15. A means to transfer torque within a pressurized device comprising:
- (a) a pressure vessel,
- (b) a spindle within said pressure vessel which is driven to rotate while in contact with a sample liquid to be measured,
- (c) a movable piston without fluid passing through its center inside of said pressure vessel with one side in contact with said sample liquid and the other side in contact with a pressurization fluid,
- (d) a seal means in contact with said movable piston and said pressure vessel,
- (e) a rotating shaft connected to said spindle and able to rotate together with said spindle
- (f) a hole in the said movable piston allowing said rotating shaft to pass through said movable piston, whereas wherein said movable piston
- (g) another seal in contact with said movable piston and said rotating shaft that prevents fluid exchange between said chamber filled with said fluid and said chamber filled with said sample,
- (h) a means to drive said rotating shaft to rotate.

16. The pressurized device of claim 15, wherein the pressurized device is a reactor.

17. The pressurized device of claim 15 further comprising a magnet attached to said rotating shaft and located in said chamber filled with a pressurization fluid.

18. The pressurized device of claim 17 further comprising a coupling magnet located outside of said pressure vessel, wherein the coupling magnet couples with said magnet.

19. The pressurized device of claim 15, wherein the pressurized device is a viscometer.

20. The pressurized device of claim 15 further comprising a means for measuring energy consumption of driving said spindle to rotate.

* * * * *